US00PP28760P2

(12) United States Plant Patent
Hansen

(10) Patent No.: US PP28,760 P2
(45) Date of Patent: Dec. 12, 2017

(54) ***LEUCANTHEMUM* PLANT NAMED 'SPOONFUL OF SUGAR'**

(50) Latin Name: ***Leucanthemum×superbum* (L. Burbank)**
Varietal Denomination: Spoonful of Sugar

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/530,317

(22) Filed: Dec. 21, 2016

(51) Int. Cl.
*A01H 5/02* (2006.01)

(52) U.S. Cl.
USPC ..... Plt./285

(58) Field of Classification Search
USPC ..... Plt./285
CPC ..... A01H 5/025
See application file for complete search history.

*Primary Examiner* — Kent L Bell

(57) ABSTRACT

The new Shasta daisy plant, *Leucanthemum* 'Spoonful of Sugar', is a sturdy upright mound with dark-green serrated foliage with large, free-flowering, creamy-white inflorescences just above the foliage that cover the plant nearly from the soil to the top with numerous inflorescences on short, heavily-branched stems. The new plant is useful in the landscape as a long-flowering border, in mass, as accent plants and containerized for patio or indoor use, or as a cut flower.

1 Drawing Sheet

Botanical classification: *Leucanthemum×superbum* (L. Burbank).

Variety denomination: 'Spoonful of Sugar'.

BACKGROUND OF THE INVENTION

The original *Leucanthemum×superbum*, or Shasta daisies, were bred by Luther Burbank in the late 1800's as a cross between *Leucanthemum maximum* (Ramond) D.C. with *Leucanthemum lacustre* (Broth.) Samp. The new plant, *Leucanthemum* 'Spoonful of Sugar' originated from a planned breeding program of the inventor at a wholesale perennial nursery in Zeeland, Mich., USA in the summer of 2011. The new *Leucanthemum* was a single selected seedling from a pollination of an unreleased proprietary female parent identified as K9-31-02 (not patented) and the male parent was the unreleased proprietary hybrid K9-25-01 (unpatented). The new plant was originally evaluated in the summer of 2013 and assigned the breeder number 11-03-xx. The present invention relates to a new and distinct cultivar of Shasta daisy botanically known as *Leucanthemum×superbum* and hereinafter referred to by the cultivar name 'Spoonful of Sugar'.

Asexual reproduction of the new cultivar by basal shoot cuttings and sterile shoot-tip tissue culture at the same nursery in Zeeland, Mich. as early as the summer of 2013 has demonstrated that the new cultivar reproduces true to type with all of the characteristics of the original plant retained through successive generations of asexual propagation.

BRIEF SUMMARY OF THE INVENTION

The new plant, *Leucanthemum* 'Spoonful of Sugar', is most closely compared to the *Leucanthemum* 'Snowcap' (not patented) in habit, *Leucanthemum* 'Real Galaxy' U.S. Plant Pat. No. 23,873 in inflorescence color, and 'Whoops-a-Daisy' U.S. Plant Pat. No. 27,259 in free-flowering. In test trials in Zeeland, Mich. *Leucanthemum* 'Spoonful of Sugar' had a compact, short, dense, dome-like, rounded habit in flower. 'Spoonful of Sugar' also has broad, flat, creamy-white flower heads of two rows of ray flowers. Compared with 'Snowcap' (not patented) the new Shasta daisy has broader flower heads, and the ray florets are more creamy white and not as pure white. Compared with 'Whoops-a-Daisy' the new plant has slightly larger inflorescences and the ray florets are more creamy white. Compared with 'Sonnenschein' (not patented) the new plant is shorter with more compact flowering and the ray florets more creamy white and less yellow. Compared with 'Real Galaxy' the new plant is considerably shorter and more compact and the ray florets are not as fringed and thin. Comparisons to the parents are not possible as neither parent still exists.

*Leucanthemum* 'Spoonful of Sugar' differs from all cultivars known to the inventor in the following combined traits:

1. Sturdy plants with dark-green serrated foliage and strongly branched stems.
2. Low, mounded habit with large inflorescences covering just above the foliage from the top of the plant to the ground.
3. Flowering with numerous axillary heads on branched stems.
4. Double row of wide ray florets of creamy white.
5. Freely flowering, not requiring vernalization period for flower initiation.

BRIEF DESCRIPTION OF THE PHOTOGRAPHS

The photographs of the new plant demonstrate the overall appearance and landscape qualities of the new plant, including the unique traits. The colors are as accurate as reasonably possible with color reproductions. Ambient light spectrum, source, direction and temperature may cause the appearance of minor variation in color. The drawings are of a two-year-old plant grown in a full-sun trial garden in Zeeland, Mich.

DETAILED BOTANICAL DESCRIPTION

Figure 1:
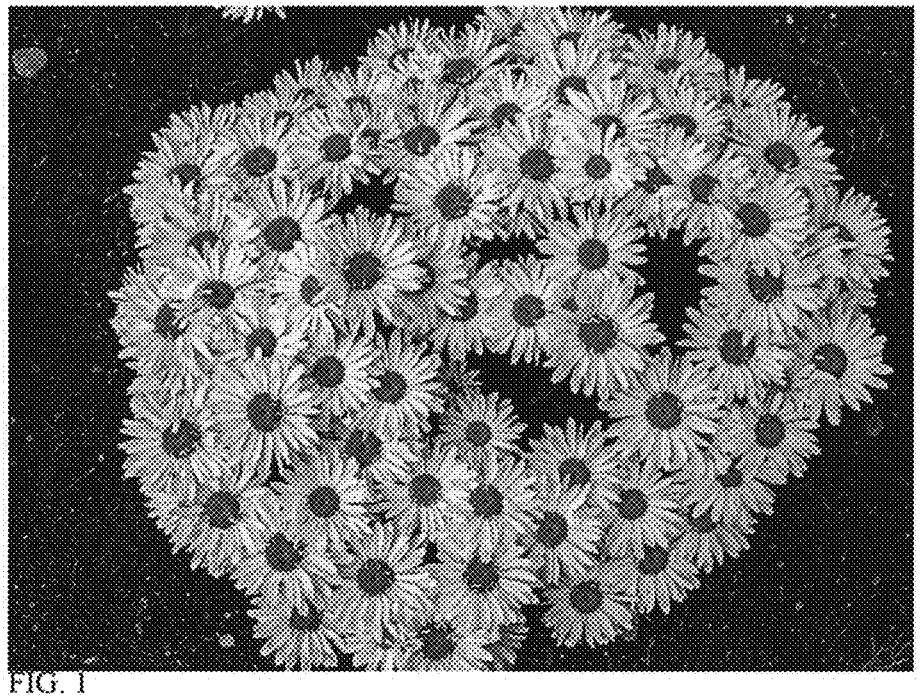
FIG. 1 Shows the new plant at peak flowering from above with inflorescences covering the plant from nearly top to ground.
Figure 2:
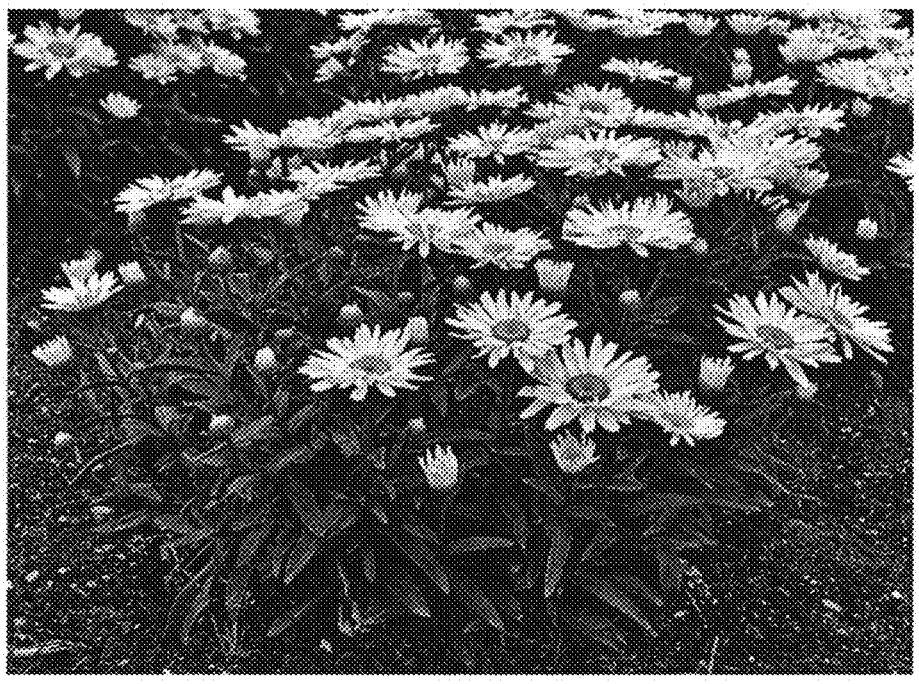
FIG. 2 Shows a side view of the new plant in early stages of flowering.

The following descriptions and color references are based on the 2001 edition of The Royal Horticultural Society Colour Chart except where common dictionary terms are used. The new plant has not been observed in all possible environments and conditions. The phenotype of *Leucanthemum* 'Spoonful of Sugar' may vary with different growing conditions such as changes in temperature, light intensity, water availability, fertility, but without change in the genotype.

The plants used for description purposes were two-year-old plants and were grown in Zeeland, Mich. in a full-sun, loamy-sand trial plot environment with supplemental water and limited fertilizer as needed. Summer temperatures range from night lows of about 10° C. to daytime highs of about 34° C. Measurements and numerical values represent averages of trial plants.

Botanical classification: *Leucanthemum* ×*superbum* (L. Burbank).

Parentage: Female parent unreleased proprietary seedling K9-31-02 (not patented); male parent the unreleased proprietary hybrid K9-25-01 (not patented).

Habit: Herbaceous perennial with about 35 branched stems arising from rhizome base; each stem having about three to four inflorescences, rarely two; about 35.0 cm tall and 60.0 cm across with rounded top and sides; flowering from top to nearly soil level.

Roots: Fibrous, thin, heavily branched; root color nearest RHS 155D depending on soil type.

Propagation: tip cuttings or tissue culture; about two weeks to produce roots from cutting; about 33 weeks to finish to flower in 3.8 liter pot depending on season.

Stems: About eighty main stems per plant, strong, upright and angled, 7.0 mm diameter at base, 30.0 cm tall; canaliculated, hispidulous; about 15 nodes, average internode length about 2.0 cm.

Stem color: Between RHS 139B and RHS 137B.

Axillary branches: Three to four, rarely two per main stem; between 6 to 10 cm long and 4 mm diameter; less canaliculated than main stem, sparsely hispidulous; at angles of about 30° from vertical main stem.

Axillary branch color: Between RHS 139B and RHS 137B.

Leaves: Lanceolate; apex acute; base sessile to attenuate, partially clasping; glabrous above, glabrous below except for main veins sparsely hispidulous, serrate with about 16 to 20 teeth per side in lowest leaves and 8 teeth in most distal leaves, more closely arranged in distal portion of leaf; teeth about 1.0 mm long; lowest leaves about 8.0 cm long and about 12.0 mm wide, distal leaves about 5.0 cm long and about 1.0 cm wide, average about 6.5 cm long and about 1.1 cm wide.

Leaf color: Adaxial color nearest RHS 137A, abaxial color between RHS 137A and RHS 137B; no fragrance detected.

Veins: Major secondary veins anastomosing, glabrous; adaxial slightly recessed.

Vein color: Abaxial midrib nearest RHS 144A and secondary veins nearest RHS 138A toward base becoming same as surrounding leaf tissue in proximal half; adaxial midrib between RHS N144A and RHS 144A, secondary veins nearest RHS 138B on adaxial side.

Inflorescence: Capitate, about 120 per plant; primary inflorescence about 10.0 cm across and about 1.5 cm tall, axillary inflorescences 8.5 cm across and 1.2 cm tall; comprising about 96 ray florets and about 800 disc florets; individual inflorescence lasting about two weeks on or cut from plant.

Fragrance: Slightly musty with age.

Flowering period: Early summer to late summer in Michigan; for about four weeks with initial flowering and followed up immediately with another three weeks.

Peduncle: Strong, sparsely hispidulous; slightly canaliculated at base, more intense canaliculated just below inflorescence; about 5.0 cm to 7.5 cm long and 2.0 to 3.0 mm diameter at base above foliage.

Peduncle color: Nearest RHS 137C.

Bud: With ray florets still vertical, adaxial and abaxial ray florets about 2.5 cm tall and about 2.0 cm across; color between RHS 155D and RHS 158D.

Ray florets: Arranged around perimeter of capitulum in at least two overlapping rows; to about 3.7 cm long and 10.0 mm wide; lanceolate; glabrous abaxial and adaxial; acute apex doubly emarginate, producing center lobe about 1.0 mm long and 2.0 mm wide at base, and two others on either side about 1.0 mm long and 1.2 mm wide at base; base attenuate, margin entire; to about 3.7 cm long and 10.0 mm wide.

Ray floret color: Are first at 180° horizontal adaxial slightly lighter than RHS 155D and abaxial lighter than RHS 155D; mature adaxial nearest RHS 155B and abaxial lighter than RHS 155D; base 10.0 mm on adaxial side and 12.0 mm on abaxial side nearest RHS 145B.

Disc florets: Combined about 2.6 cm across and about 1.5 cm tall; individual floret about 8.0 mm tall and 1.2 mm wide, five pointed, about 3.0 mm long with acute apex, fused at base.

Disc floret color: Base between RHS 146 C and RHS 146B; apical 3 mm of RHS 13A.

Androecium: Only in disc florets; five stamens connate around style.

*Anther*.—About 2.0 mm long and less than one mm wide, anther coloration nearest RHS 17A.

*Filaments*.—Fused together at base, about 2.0 mm long and less than 0.1 mm diameter, filament coloration nearest RHS 2D.

Gynoecium: In ray florets and disc florets.

*Style*.—About 5.0 mm long and about 0.5 mm diameter, split and curved at apical 1.0 mm; color nearest RHS 154D.

*Stigma*.—Less than 0.5 mm diameter; color between RHS 17D and RHS 17C.

Involucre: Made of about three layers of phyllaries averaging 48 per head; to 3.0 across and 0.5 cm tall.

Phyllaries: Glabrous; entire margin, apex acute, base truncate; 10.0 mm long and 3.0 mm wide.

Phyllaries color: Nearest RHS 145A on abaxial and adaxial center portions and between RHS 144A and RHS 144B in the crosswise center portions and base; distal phyllaries with a 1.0 mm wide margin in the apical 3.0 mm or nearest RHS 166A.

Fruit: Achene, pointed at base and rounded at distal end with longitudinal color striations nearest RHS N200A and lighter than RHS 155D; about 3 to 4 mm long and 1.5 mm across.

*Leucanthemum* 'Spoonful of Sugar' grows best with adequate moisture but can tolerate some dryness once established. It is tolerant of high temperatures of at least 36° and cold hardy to at least USDA zone 5 as well as strong wind and rain. Other disease or pest resistance beyond that common to Shasta daisy has not been observed.

It is claimed:

1. A new and distinct *Leucanthemum* plant named 'Spoonful of Sugar' as herein illustrated and described.

* * * * *